United States Patent [19]

Yoo

[11] Patent Number: 5,933,685
[45] Date of Patent: Aug. 3, 1999

[54] APPARATUS FOR DETECTING CONCENTRATION OF DEVELOPER BY MEASUREMENT OF OPTICAL TRANSMISSIVITY

[75] Inventor: Yong-Baek Yoo, Suwon, Rep. of Korea

[73] Assignee: Samsung Electronics Co., Ltd., Kyungki-do, Rep. of Korea

[21] Appl. No.: 09/072,693

[22] Filed: May 6, 1998

[30] Foreign Application Priority Data

Jul. 16, 1997 [KR] Rep. of Korea .................... 97-33254

[51] Int. Cl.⁶ .......................... G03G 15/10; G01N 21/47
[52] U.S. Cl. ................................. 399/57; 399/65
[58] Field of Search ................... 399/57, 58, 62, 399/64, 65, 239–45; 118/690, 691

[56] References Cited

U.S. PATENT DOCUMENTS 4,204,766  5/1980  Harada ..................................... 356/404
5,724,629  3/1998  Iino et al. ................................. 399/57

FOREIGN PATENT DOCUMENTS 53-3348    1/1978   Japan .
5-232821   9/1993   Japan .
5-332926  12/1993   Japan .

*Primary Examiner*—Joan Pendegrass
*Attorney, Agent, or Firm*—Sughrue, Mion, Zinn, Macpeak & Seas, PLLC

[57] ABSTRACT

A developer concentration detection apparatus is provided, which includes a base member in which a developer accommodation space is formed, an electrode plate member installed in the base member so that a toner included in a developer in the developer accommodation space is electrically charged, a hollow transparent conductive tube which is rotatably supported in the state where at least part thereof is submerged in the developer in the developer accommodation space and the surface thereof can be charged, a light emitting element installed in the transparent conductive tube, and a light receiving element installed spaced from the surface of the transparent conductive tube, for detecting light generated from the light emitting element. The developer concentration detection apparatus can detect measurement of the developer concentration, thereby providing the result of assuring an optimal printing quality. Also, reliability and accuracy of the measurement is guaranteed since the developer concentration is measured by directly detecting the amount of the particles of the toner included in the developer.

7 Claims, 3 Drawing Sheets

APPARATUS FOR DETECTING CONCENTRATION OF DEVELOPER BY MEASUREMENT OF OPTICAL TRANSMISSIVITY

BACKGROUND OF THE INVENTION

1. Field of the Invention

The present invention relates to a developer concentration detection apparatus, and more particularly, to a developer concentration detection apparatus which can measure a concentration of a developer by measuring an optical transmissivity of a developer in an electrophotographic printer.

2. Description of the Related Art

Generally, a photosensitive medium such as a photosensitive belt or photosensitive drum is used in an electrophotographic printer. As is known, the surface of the photosensitive medium can be charged and the level of the electric potential can be selectively changed by a scanned beam, thereby forming an electrostatic latent image. The printers are divided into a dry type and a wet type according to the state of a toner attached to the electrostatic latent image. In a wet type printer, a developer obtained by mixing a liquid toner and a carrier is used in printing.

FIG. 1 shows a schematic view of a general wet type color printer. Referring to FIG. 1, the printer includes a photodetection belt 14 which is supported by a driving roller 11, a direction control roller or tension roller 12, and a counter roller 13, and rotates along an endless track, at least one of the developing units 17a, 17b, 17c and 17d, and an image transfer roller 25. The photodetection belt 14 can be maintained in a state where the surface thereof has been charged by a corona apparatus 16. The charged state of the photodetection belt 14 can be changed in electric potential as laser beams are scanned from laser scanning units 18a, 18b, 18c and 18d which are closely installed to the respective developing units 17a, 17b, 17c and 17d. The beams scanned from the laser scanning units 18a, 18b, 18c and 18d form latent images on the surface of the photodetection belt.

The developing units 17a, 17b, 17c and 17d can develop colors of black, yellow, cyan and magenta, according to the paint color. Also, the laser scanning units 18a, 18b, 18c and 18d can form latent images with respect to corresponding colors. Developers are filled in the developing units 17a, 17b, 17c and 17d. The developer can be attached to a latent image formed on the surface of the photodetection belt 14 via a developing roller (not shown) provided in each developing unit. A backup roller (not shown) is mounted in correspondence to each developing roller (not shown). A cleaning roller 23 has the function of completely removing the carrier from the toner image formed on the photodetection belt 14. A heating roller 24 evaporates the carrier in order to assist the function of the cleaning roller 23. The toner image attached to the photodetection belt 14 is transferred to the image transfer roller 25, so that the image can be transferred from the image transfer roller 25 to paper 27. The printing paper 27 passes between the image transfer roller 25 and a fixing roller 26. An erasure 15 performs the function of completely removing the charging state remaining on the photodetection belt 14, to thereby form a new electrostatic latent image.

The developer filled in each developing unit 17a, 17b, 17c or 17d is a mixture of a toner and a carrier. The toner is stored in toner containers 19a, 19b, 19c and 19d, and supplied to a mixture containers 21a, 21b, 21c and 21d via pumps 20a, 20b, 20c and 20d, respectively. The carrier is stored in a carrier container 28, and supplied to mixture containers 21a, 21b, 21c and 21d, respectively. The mixture containers 21a, 21b, 21c and 21d mix the toner and carrier at a proper concentration and supply the mixed result to each developing unit 17a, 17b, 17c or 17d via the pumps 22a, 22b, 22c and 22d. The carrier container 28 also stores the carrier returning from the cleaning apparatus including the cleaning roller 23 and the heating roller 24.

In the above printer, the concentration of the developer supplied to each developing unit 17a, 17b, 17c or 17d should be maintained constant. That is, a ratio of the mixture of the toner and carrier should be maintained properly. This is performed by controlling the amount of liquid supplied from the toner containers 19a, 19b, 19c and 19d and the carrier containers 28 to the mixture containers 21a, 21b, 21c and 21d, respectively. Also, in order to control a ratio of the mixture of the toner and carrier, an apparatus for detecting a concentration of the developer should be provided. According to the prior art, developer concentration detection apparatuses are disclosed in U.S. Pat. Nos. 4,310,238 (Ricoh) and 5,570,193 (Indigo). These apparatuses are not widely used since the measuring method is changed according to the characteristic of the developer.

SUMMARY OF THE INVENTION

To solve the above problem(s), it is an objective of the present invention to provide a developer concentration detection apparatus which can detect a concentration of a developer.

It is another object of the present invention to provide an apparatus for detecting a concentration of developer by measuring an optical transmissivity of the developer, and allows a user to predict the density of an image to be printed on paper.

It is still another object of the present invention to provide a developer concentration detection apparatus provided in an electrophotographic printer. Accordingly, to achieve the above objective, there is provided a developer concentration detection apparatus comprising: a base member in which a developer accommodation space is formed; an electrode plate member installed in the base member so that a toner included in a developer in the developer accommodation space is electrically charged; a hollow transparent conductive tube which is rotatably supported in a state where at least part thereof is submerged in the developer in the developer accommodation space and the surface thereof can be charged; a light emitting element installed in the transparent conductive tube; and a light receiving element installed spaced from the surface of the transparent conductive tube, for detecting light generated from the light emitting element.

According to one aspect of the present invention, the developer concentration detection apparatus further comprises a microprocessor in which a concentration of developer corresponding to the amount of light detected from the light receiving element is pre-stored.

According to another aspect of the present invention, the developer concentration detection apparatus further comprises a cleaning roller installed at one side of the transparent conductive tube and a carrier liquid supply nozzle installed close to the transparent conductive tube.

According to still another aspect of the present invention, the toner included in the developer in the developer accommodation space is attached to the surface of the charged transparent conductive tube after the toner has been charged by the charged electrode plate member.

According to yet another aspect of the present invention, the light generated from the light emitting element is transmitted through the transparent conductive tube and the toner attached to the surface of the transparent conductive tube, and is detected at the light receiving element.

According to still yet another aspect of the present invention, the transparent conductive tube is obtained by coating an indium-tin-oxide (ITO) coating thin film on the surface of a hollow tube made of glass.

According to a further aspect of the present invention, a developer discharge path which can be opened and closed, is formed on the bottom of the developer accommodation space.

BRIEF DESCRIPTION OF THE DRAWING(S)

The above objectives and advantages of the present invention will become more apparent by describing in detail a preferred embodiment thereof with reference to the attached drawings in which.

DESCRIPTION OF THE PREFERRED EMBODIMENT(S)

The present invention will be described below with reference to the attached drawings.

Figure 2:
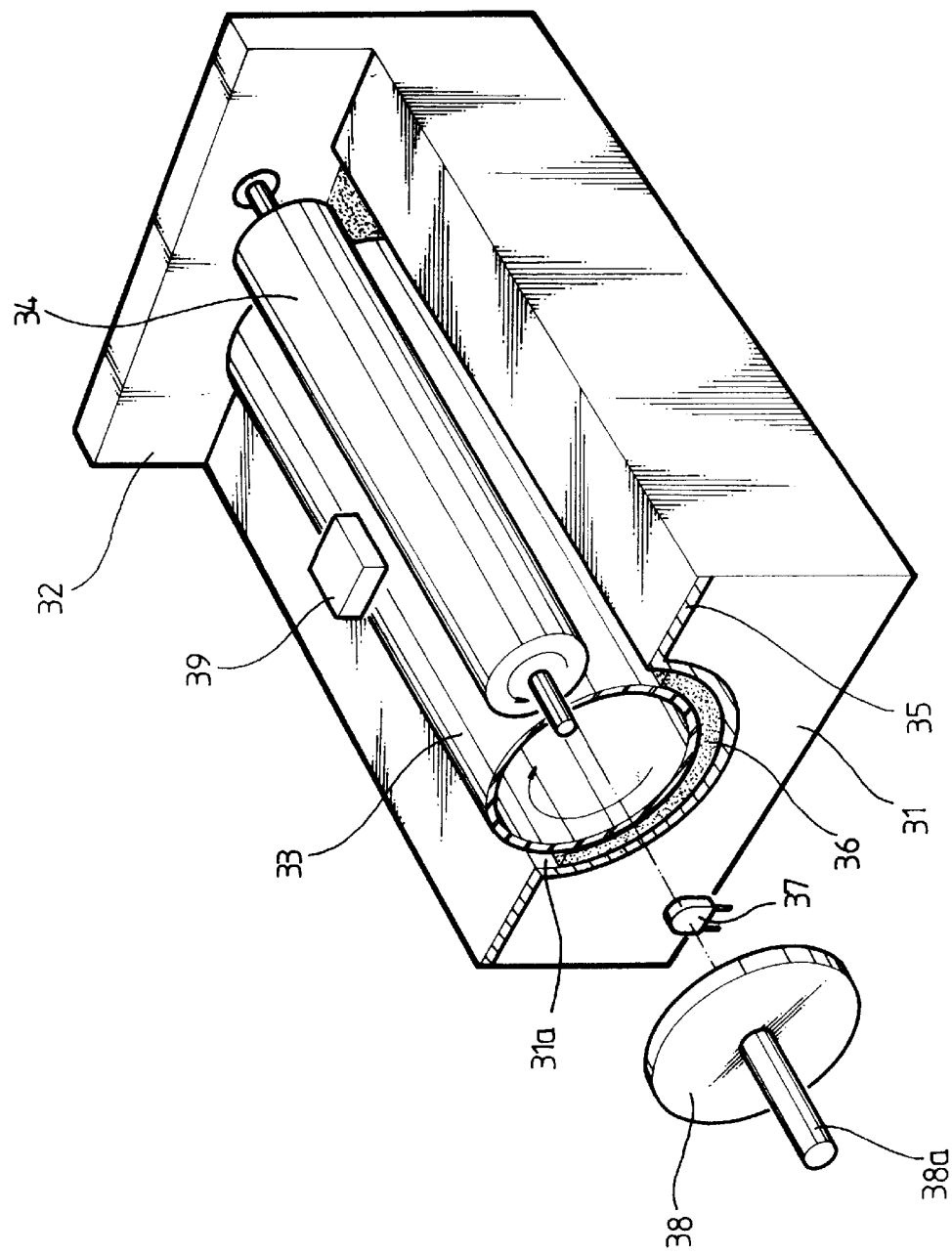
FIG. 2 is a schematic perspective view of part of a developer concentration detection apparatus according to the present invention.
Figure 3:
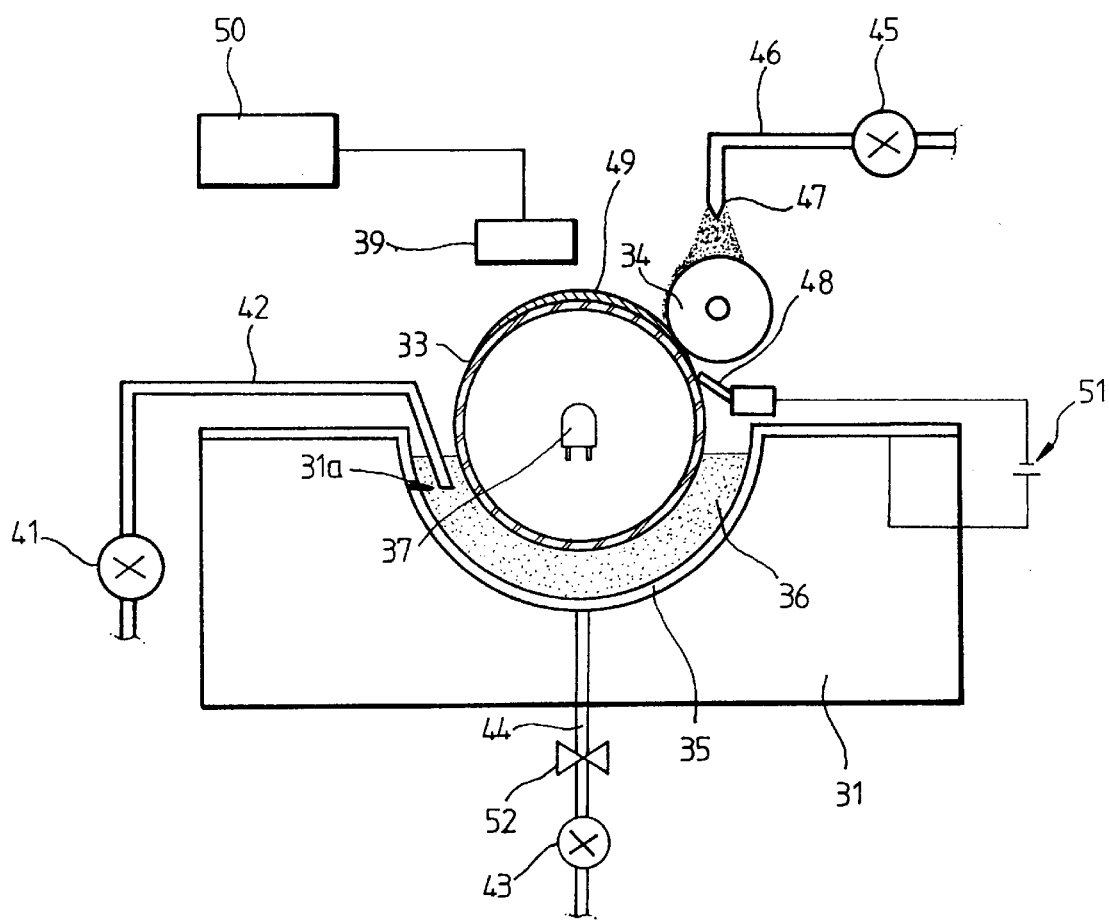
FIG. 3 is a schematic view of a developer concentration detection apparatus according to the present invention.

The same reference numerals of FIGS. 2 and 3 are assigned to the same elements for convenient explanation. The present invention is disclosed in FIG. 2, which discloses part of a developer concentration detection apparatus, and FIG. 3, which discloses a developer concentration detection apparatus. In the present invention (see FIG. 2), a developer accommodation space 31a is formed in a base 31. A transparent conductive tube 33 and a cleaning roller 34 are rotatably supported on the side wall 32 of the base 31. As shown in the drawings, it is preferable that the cross section of the developer accommodation space 31a is formed as a semi-circle. A developer 36 is accommodated therein in proper depth. It is preferable that the developer 36 is accommodated in the developer accommodation space 31a so that at least part of the transparent conductive tube 33 is submerged into the developer 36. The surface of the base 31 should be formed of an electrode plate 35. The surface corresponding to the portion which forms the developer accommodation space 31a among the surface of the base 31 should be formed of the electrode plate 35. This is because the toner in the developer 36 accommodated in the developer accommodation space 31a is charged to a predetermined electric potential.

The transparent conductive tube 33 is made by forming an ITO coating thin film on the surface of glass, for example. Since the ITO coating thin film formed on the surface of the transparent conductive tube 33 has a conductivity, it can be charged to a predetermined electric potential when power is applied thereto. The transparent conductive tube 33 can be rotated by a rotational drive unit (not shown). A light emitting element 37 is installed in the hollow transparent conductive tube 33. For example, a laser diode or light emitting diode can be used as a light emitting element 37. Either end of the transparent conductive tube 33 is closed by a lid 38. A rotational shaft 38a is installed on the lid 38. Accordingly, the transparent conductive tube 33 is rotatably supported with respect to the side wall 32 of the base 31.

As will be described in more detail later, the light generated from the light emitting element 37 is transmitted by the transparent conductive tube 33 and the toner attachment portion attached to the surface of the transparent conductive tube 33. The transmitted light is detected by the light receiving element 39. Accordingly, the amount of the corresponding transmitted light can be detected. The light receiving element 39 is installed spaced by a predetermined distance from the surface of the transparent conductive tube 33.

The cleaning roller 34 is installed at one side of the transparent conductive tube 33. The cleaning roller 34 is installed to contact the transparent conductive tube 33, by which the cleaning roller 34 can be rotated by friction due to rotation of the transparent conductive tube 33. Otherwise, a separate drive unit (not shown) is provided to allow the cleaning roller 34 to rotate voluntarily. The cleaning roller 34 has the function of cleaning the surface of the transparent conductive tube 33. That is, since the cleaning roller 34 contacts the surface of the transparent conductive tube 33, the developer 36 attached to the surface of the transparent conductive tube 33 can be removed.

Referring to FIGS. 2 and 3, the transparent conductive tube 33 can rotate clockwise and the cleaning roller 34 contacting the transparent conductive tube 33 can rotate counterclockwise. Power is applied from a power supply 51 to the electrode plate 35 formed on the surface of the base 31 and the conductive thin film formed on the surface of the transparent conductive tube 33, which are thus charged to a predetermined electric potential. For example, the transparent conductive tube 33 is charged by means of a brush 48 which is installed to contact the surface thereof. The charged electrode plate 35 charges toner particles of the developer 36. The charged toner particles can be attached to the ITO coating thin film of the charged transparent conductive tube 33, which is charged at a different polarity. Reference numeral 49 denotes a toner attachment portion.

Figure 1:
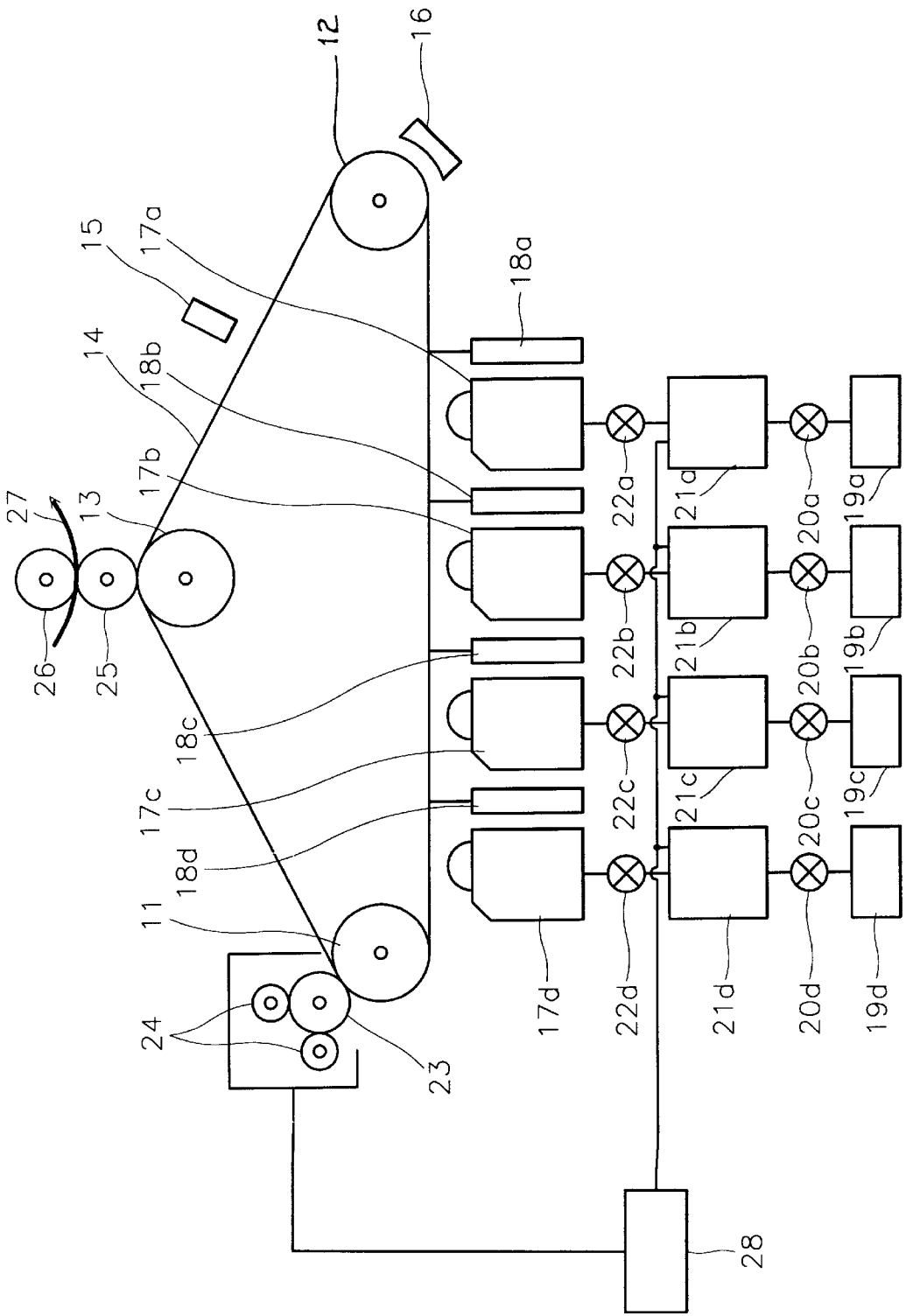
FIG. 1 is a schematic view of a general electrophotographic printer.

The charged developer 36 can be supplied into the developer accommodation space 31a via a supply tube 42 by a supply pump 41. The developer 36 supplied via the supply tube 42 should be the same as that used for printing in the developing units 17a, 17b, 17c and 17d of FIG. 1. Thus, it is preferable that the developer 36 supplied via the supply tube 42 is supplied via a separate fluid path from the mixture containers 21a, 21b, 21c and 21d. In an alternative embodiment, the concentration detection apparatus according to the present invention can be integrally formed along with a mixture container.

As described above, the light generated in the light emitting element 37 installed in the transparent conductive tube 33 is transmitted through the transparent conductive tube 33 and the toner attachment portion 49, and is detected by the light receiving element 39. The data with respect to the transmitted light amount which has been detected in the light receiving element 39 is compared with a concentration with respect to the transmitted light amount which has been input in advance from the microprocessor 50, which can allow a concentration of a corresponding developer to be detected.

For example, when a concentration of a developer is high, the number of the particles of the toner included in the developer becomes larger. Thus, it can be seen that the number of the particles of the toner attached to the surface of the transparent conductive tube 33 increases relatively. In this case, the light amount detected in the light receiving element 39 decreases relatively, and the concentration of the developer is relatively high.

Conversely, when a concentration of the developer is low, the number of toner particles attached to the surface of the transparent conductive tube 33 will decrease relatively, and the light amount reaching the light receiving element 39 via the transparent conductive element will increase.

Thus, it can be seen that the developer concentration is low from the increase of the light amount detected in the light receiving element 39. Of course, the data with respect to the concentration of the developer 36 corresponding to the respective light amount should be input to the microprocessor 50 in advance. Also, the developer concentration can be detected by comparing the detected light amount with the pre-stored data.

After detecting the transmitted light amount via the light emitting element 37 and the light receiving element 39, the cleaning roller 34 performs the function of removing the toner attached to the surface of the transparent conductive tube 33. The cleaning roller 34 closely contacts the surface of the transparent conductive tube 33, to thereby remove the toner attached to the surface of the transparent conductive tube 33. In removing the toner, carrier liquid is selectively used.

The carrier liquid can be supplied via the supply tube 46 by the supply pump 45, and sprayed to the surface of the cleaning roller 34 or the transparent conductive tube 33 via a nozzle 47. When using the carrier liquid for removing the toner, the carrier liquid stored in the carrier container 28 is supplied 20 via a separate fluid path. Once the carrier liquid has been sprayed, the concentration of the developer contained in the developer accommodation space 31a is changed. Accordingly, a further measurement of the developer concentration is meaningless. The spraying of the carrier liquid dilutes the toner, to thereby perfectly clean the surface of the transparent conductive tube 33. Accordingly, spraying of the carrier liquid is selectively performed after measurement of the transmitted light amount is completed. That is, the carrier liquid is sprayed so that a subsequent concentration measurement can be accurately performed, to thereby conduct a perfect cleaning operation.

After having sprayed the carrier liquid, the developer accommodated in the developer accommodation space 31a is discharged via the fluid path formed on the bottom thereof. In the embodiment shown in the drawings, the developer is discharged via a discharging tube 44. The discharging tube 44 can be installed on the bottom of the developer accommodation space 31a. For example, the discharging tube 44 can be opened and closed by a solenoid valve 52. The developer 36 can be discharged by operation of the pump 43. The discharged developer 36 can be stored in a storage container (not shown) to be re-used.

Although part of the operation of the present invention has been described, the operation of the developer concentration detection apparatus according to the present invention will be described in more detail.

The developer 36 is charged in the developer accommodation space 31a of the base 31 via the supply tube 42. It is preferable that part of the surface of the transparent conductive tube 33 is submerged in the developer 36 charged in the accommodation space 31a. If power is applied to the surface of the transparent conductive tuber 33 and the electrode plate 35, the toner included in the developer 36 enters a charged state, and the charged toner is attached to the surface of the transparent conductive tube 33. If the transparent conductive tube 33 is rotated, the carrier liquid falls down due to gravity, and the toner attachment portion 49 formed of the toner exists along the optical path of the light emitting element 37. The light generated from the light emitting element 37 is transmitted via the transparent conductive tube 33 and the toner attachment portion 49, and the corresponding transmitted light is detected by the light receiving element 39. The amount of the light detected in the light receiving element 39 can be operated as a concentration of the developer 36 corresponding to the amount of the detected transmitted light in the microprocessor 50.

After the developer concentration detection operation has been performed, the carrier liquid supplied via the carrier supply tube 46 is sprayed via the nozzle 47. Simultaneously, the cleaning roller 34 closely contacts the transparent conductive tube 33, to remove the toner attached to the surface of the transparent conductive tube 33. In order to completely remove the developer 36 input to the developer concentration detection apparatus, the valve 52 should be opened. The developer 36 can be discharged via the discharging tube 44 after being pressed by the pump 43.

The microprocessor 50 performs an operation of controlling a concentration of the developer 36 supplied to the developing units on the basis of the detected concentration. That is, an optimal concentration of the developer 36 can be maintained by controlling the amount of the developer input from the toner containers 19a, 19b, 19c and 19d and the carrier container 28.

The developer concentration detection apparatus according to the present invention can detect measurement of the developer concentration, thereby providing the result of assuring an optimal printing quality. Also, reliability and accuracy of the measurement is guaranteed since the developer concentration is measured by directly detecting the amount of the particles of the toner included in the developer. Furthermore, it is possible to predict the density of an image to be printed on the paper.

The present invention has been described with respect to one embodiment shown in the accompanying drawings, which is only an illustrative example. It can be understood by a person skilled in the art that various modifications and other variations are possible therefrom. Thus, the protection scope of the present invention should be defined by the attached claims.

What is claimed is:

1. A developer concentration detection apparatus comprising:
    a base member in which a developer accommodation space is formed;
    an electrode plate member installed in the base member so that a toner included in a developer in the developer accommodation space is electrically charged;
    a hollow transparent conductive tube which is rotatably supported at the state where at least part thereof is submerged in the developer in the developer accommodation space and a surface thereof can be charged;
    a light emitting element installed in the transparent conductive tube;
    a light receiving element installed spaced from the surface of the transparent conductive tube, for detecting light generated from the light emitting element;
    a cleaning roller installed at one side of the transparent conductive tube; and
    a carrier liquid supply nozzle installed proximate to the transparent conductive tube.

2. The developer concentration detection apparatus according to claim 1, further comprising a microprocessor in which a concentration of a developer corresponding to an amount of light detected from the light receiving element is pre-stored.

3. The developer concentration detection apparatus according to claim 1, wherein said toner included in the developer in the developer accommodation space is attached to the surface of the charged transparent conductive tube after the toner has been charged by the charged electrode plate member.

4. The developer concentration detection apparatus according to claim 3, wherein said light generated from the light emitting element is transmitted through the transparent conductive tube and the toner attached to the surface of the transparent conductive tube, and is detected at the light receiving element.

5. The developer concentration detection apparatus according to claim 1, wherein said light generated from the light emitting element is transmitted through the transparent conductive tube and the toner attached to the surface of the transparent conductive tube, and is detected at the light receiving element.

6. The developer concentration detection apparatus according to claim 1, wherein said transparent conductive tube is obtained by coating an indium-tin-oxide (ITO) coating thin film on a surface of a hollow tube made of glass.

7. The developer concentration detection apparatus according to claim 1, wherein a developer discharge path which can be opened and closed is formed on a bottom of the developer accommodation space.

* * * * *